(12) United States Patent
Al Saeed et al.

(10) Patent No.: US 11,766,498 B2
(45) Date of Patent: Sep. 26, 2023

(54) SMART ELECTRIC INCENSE AND PERFUME BURNER

(71) Applicants: Faisal Faraj Al Saeed, Hadiya (KW); Mohammad Faisal Ballam, Rumaithiya (KW)

(72) Inventors: Faisal Faraj Al Saeed, Hadiya (KW); Mohammad Faisal Ballam, Rumaithiya (KW)

( * ) Notice: Subject to any disclaimer, the term of this patent is extended or adjusted under 35 U.S.C. 154(b) by 0 days.

(21) Appl. No.: 17/831,997

(22) Filed: Jun. 3, 2022

(65) Prior Publication Data
US 2022/0378969 A1    Dec. 1, 2022

Related U.S. Application Data (62) Division of application No. 17/334,666, filed on May 28, 2021, now Pat. No. 11,382,997.

(51) Int. Cl.
*H05B 3/16* (2006.01)
*A61L 9/03* (2006.01)
*B01F 23/21* (2022.01)

(52) U.S. Cl.
CPC ............... *A61L 9/037* (2013.01); *A61L 9/03* (2013.01); *B01F 23/215* (2022.01); *H05B 3/16* (2013.01); *A61L 2209/111* (2013.01); *A61L 2209/133* (2013.01)

(58) Field of Classification Search
CPC .......... H05B 3/16; A61L 19/03; A61L 19/037
See application file for complete search history.

(56) References Cited

U.S. PATENT DOCUMENTS

| | | | |
|---|---|---|---|
| 3,058,178 A | 10/1962 | Campagna |
| 6,050,551 A | 4/2000 | Anderson |
| 6,562,302 B1 | 5/2003 | Hooks, II |
| 7,046,919 B2 | 5/2006 | Shimizu et al. |
| 8,137,630 B2 | 3/2012 | Jorgensen |
| D764,079 S | 8/2016 | Wu |
| 2011/0027124 A1 | 2/2011 | Albee et al. |
| 2011/0097242 A1 | 4/2011 | Al-Mahnna |

FOREIGN PATENT DOCUMENTS

| | | |
|---|---|---|
| CN | 203329083 U | 12/2013 |
| CN | 204580836 U | 8/2015 |
| CN | 204683281 U | 10/2015 |
| ES | 1247224 U | 6/2020 |
| JP | 01003422 A * | 1/1989 |

* cited by examiner

*Primary Examiner* — Robert A Hopkins
(74) *Attorney, Agent, or Firm* — Nath, Goldberg & Meyer; Richard C. Litman (57) ABSTRACT

The smart electric incense and perfume burner is a remotely controllable, electrical incense burner controllable via a smart system using Wi-Fi or Bluetooth. The burner is in the form of an orb or spherical shell, which may be placed on top of a pedestal having a battery charging circuit. The orb functions separately as a portable, battery-operated, smart electric incense and perfume burner. The orb includes an upper chamber, centrally located at the top of the orb for liquid incense or perfume. The orb also includes a lower chamber with a solid incense heater. The outer surface of the orb has a plurality of vent openings for allowing smoke from the upper and lower chambers to exit the interior of the orb. The vent openings are surrounded by multicolor LEDs and are adapted to receive elongated decorations for display.

1 Claim, 13 Drawing Sheets

SMART ELECTRIC INCENSE AND PERFUME BURNER

This is a Divisional Application of U.S. patent application Ser. No. 17/334,666, filed May 28, 2021, the contents of which are hereby incorporated by reference in their entirety.

BACKGROUND

1. Field

The disclosure of the present patent application relates to aromatic dispensers, and particularly to a smart electric incense and perfume burner.

2. Description of the Related Art

In general, incense and perfume burners are known and are referred to as censers, vessels, incense burners or perfume burners. Early Islamic vessels from the 11th century until the Mongol conquests of the 13th century were usually called perfume burners and had no specific religious function, although they were widely used in homes. These vessels were often in animal shapes, such as lynx or other felines, and were made of bronze or brass with open framework bodies. A wide variety of other types have been used over the years. Presently, modern incense or perfume burners are mostly made of wood or metal. The heat for activating the incense or perfume is provided by burning coals or gas, or by electrical power. The greatest shortcoming of these devices is that they pose a fire hazard, particularly for the coal and gas burners. Even the electrical burners may pose a fire hazard. These incense or perfume burners do not include safety measures to shut off the burner when excessive temperatures, smoke, or tilting of the burner occurs.

Thus, a smart electric incense and perfume burner solving the aforementioned problems is desired.

SUMMARY

The smart electric incense and perfume burner is a remotely controllable electrical incense burner that may be controlled via a smart system using Wi-Fi or Bluetooth. The burner may be in the form of an orb or a substantially spherical shell or other shape, which may be placed on top of a pedestal having a battery charging circuit. The orb functions as a portable, battery-operated, smart electric incense and perfume burner when it is not on the pedestal. The orb includes an upper chamber centrally located at the top of the orb for receipt of a capsule of liquid incense or perfume, the capsule having a wick and a heating element. A first electrical linear actuator retracts the upper chamber into the orb or extends it above the top of orb for insertion of the capsule. The top of the upper chamber includes programmable control buttons. The orb also includes a lower chamber for solid incense. The lower chamber is in the form of an electrically retractable drawer that extends and retracts through an opening near the bottom of the orb. A second electrical linear actuator extends and retracts the lower chamber into and out of the orb. The top surface of the lower chamber has a protective mesh cover that prevents any solid incense debris from coming out of the lower chamber. A solid incense heater in the lower chamber having two heating coils sandwiched between two mica sheets is used to heat the solid incense. The solid incense heater may have uses other than heating incense for the smart electric incense and perfume burner.

The outer surface of the orb has a plurality of vent openings for allowing smoke from the upper and lower chambers to exit the interior of the orb. The vent openings may be adapted to receive flowers or other elongated decorations for display. Each of the vent openings is surrounded by a hollow, frustoconical, acrylic housing with internal multicolor LEDs that define a central opening. The orb includes an upper portion or cover that houses the upper chamber and has an outer surface in the shape of a partial sphere. The orb also includes a central portion or housing that houses a dual electric fan assembly and a lower portion or orb base that houses the lower chamber and has a flat bottom for resting the orb on horizontal surfaces when the orb is not on the pedestal. A circular slot is formed between the orb cover and the central housing. The dual fan assembly directs smoke from the lower chamber out of the plurality of vent openings and the circular slot. The orb base also houses the batteries, battery management systems, a microcontroller, and smoke/temperature sensors for controlling the various functions of the burner.

The pedestal includes a charging circuit having an AC/DC converter and a relay component for providing charging DC power to the orb. The pedestal may also include optional features, such as Wi-Fi and Bluetooth devices, such that the smart electric incense and perfume burner can be turned on and controlled remotely thru a smart phone app or using smart home devices, such as Google Home or Amazon Alexa, as well as a media player for radio, IOS, and Android devices. The top surface of the pedestal includes an on/off button, while the front of the pedestal may also include an optional incense storage drawer.

These and other features of the present subject matter will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
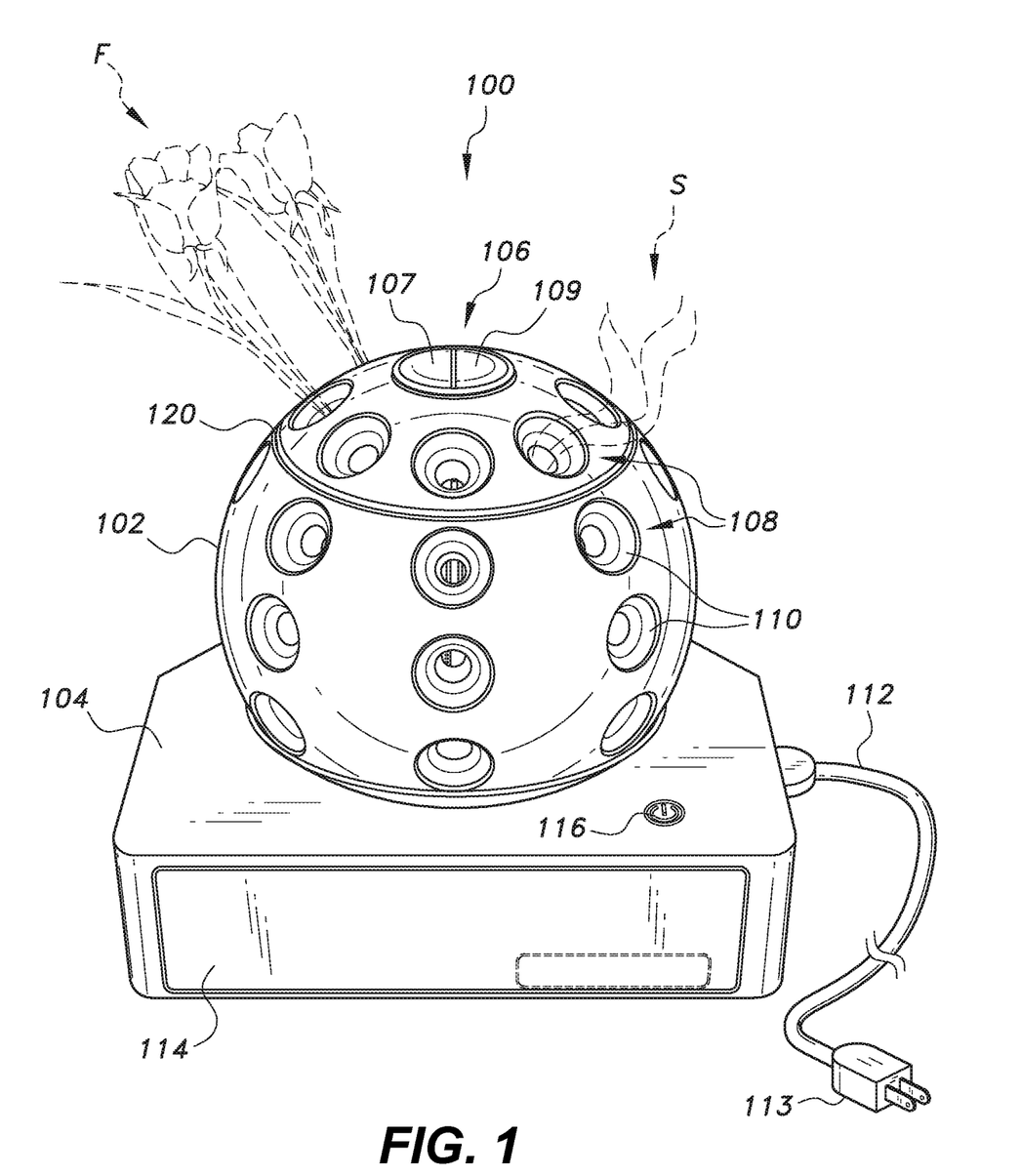
FIG. 1 is a perspective view of a smart electric incense and perfume burner mounted on the pedestal, as viewed from the front of the pedestal.
Figure 2:
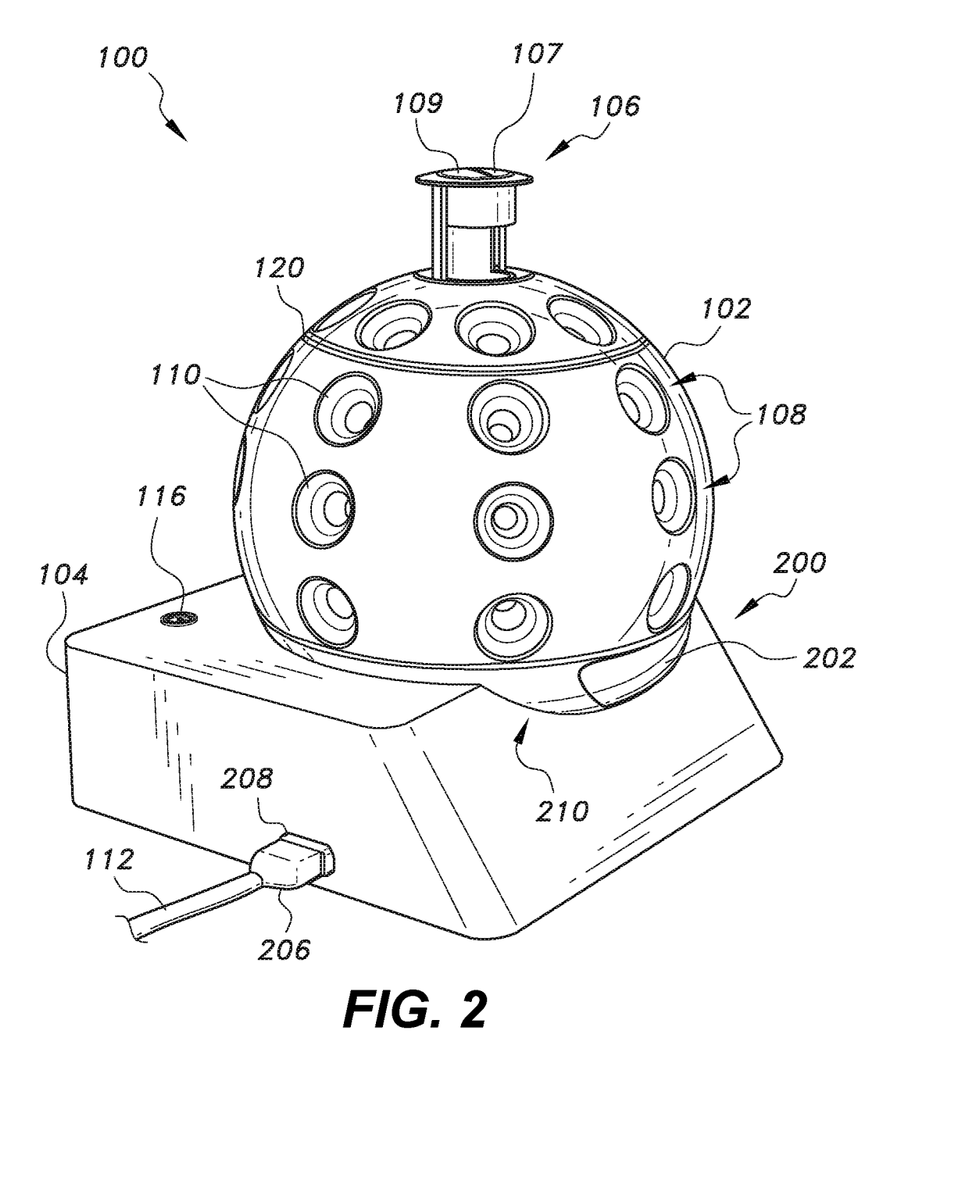
FIG. 2 is perspective view of the smart electric incense and perfume burner of FIG. 1, as viewed from the rear of the pedestal on its pedestal.

The smart electric incense and perfume burner 100 is shown generally in FIGS. 1-2. The burner 100 includes an orb or substantially spherical housing 102, which is shown received in and resting upon a pedestal 104. The orb 102 functions as a portable, battery-operated, smart electric incense and perfume burner when it is not on the pedestal 104. The details of the pedestal 104 are described below with respect to FIGS. 1, 2, 15, and 16.

The orb 102 includes an upper chamber 106 centrally located at the top of the orb 102 for receipt of a capsule of liquid incense or perfume, the capsule having a wick and a heating element, as described further below with respect to FIG. 9. The top surface of the upper chamber 106 includes at least two semicircular, programmable push-buttons 107, 109, although others may be added as desired. The push-buttons 107, 109 are connected to a microprocessor for activating various functions, as described further below. The upper chamber 106 is shown in its retracted, lower position in FIG. 1, and in its extended, raised position in FIG. 2. The orb 102 also includes a lower chamber 200, shown in its retracted position in FIG. 2. The lower chamber 200 is used for solid incense, as described below with respect to FIGS. 10-14, where the lower chamber 200 is shown in its extended position. The outer surface of the orb 102 has a plurality of vent openings 108 for allowing smoke S from the upper 106 and lower 200 chambers to exit the interior of the orb 102. The openings 108 may be adapted to receive flowers F or other elongated decorations for display. Each of the vent openings 108 is surrounded by a hollow, frustoconical, acrylic housing 110 with internal LEDs and a central opening. The LEDs are multicolor LEDs and are provided for both illumination and aesthetic purposes.

Figure 3:
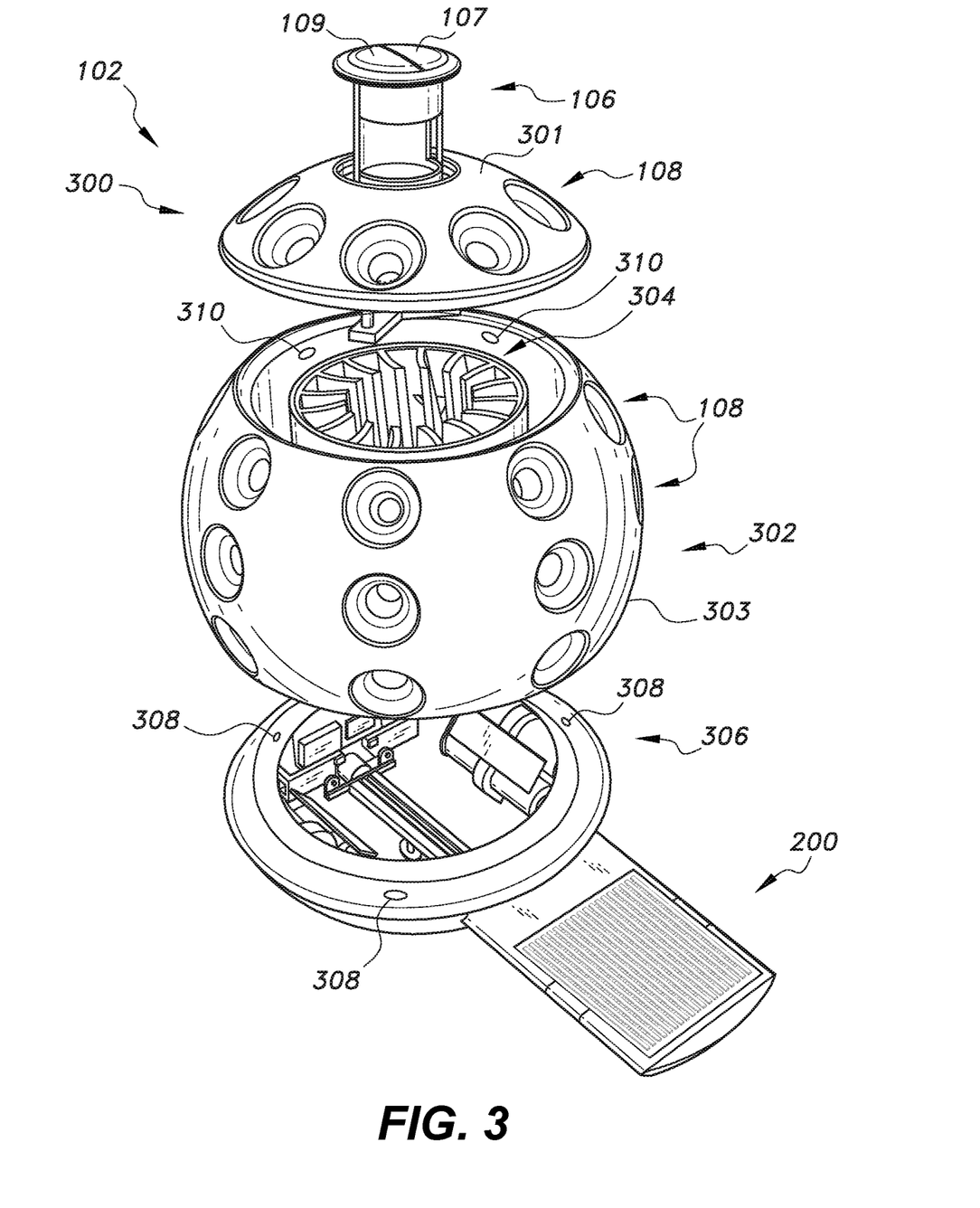
FIG. 3 is an exploded perspective view of the smart electric incense and perfume burner of FIG. 1, shown removed from the pedestal.

The orb 102 is shown in an exploded view in FIG. 3. The orb 102 includes an upper portion or cover 300 that has an upper, outer surface 301 in the shape of a partial sphere. The cover 300 houses the upper chamber 106, as described further below with respect to FIGS. 6-7. The orb 102 also includes a central portion or housing 302 with an outer surface 303 in the form of a sphere that is truncated at both its top and bottom to form flat top and bottom surfaces. The central housing 302 houses a dual fan assembly 304 that is described below with respect to FIGS. 4-5. The orb 102 further includes a lower portion or orb base 306. The orb base 306 houses the lower chamber 200 (shown in its extended position in FIG. 3) as described below with respect to FIGS. 10-14. The cover 300, the central housing 302 and the orb base 306 may be fastened to one another, or simply stacked on one another, as shown. In some embodiments, magnets 308 and mating metal discs 310 may be provided for releasably connecting the cover 300, the central housing 302 and the orb base 306 together. A circular slot 120, shown in FIGS. 1-2, is formed at the junction of the cover 300 and the central housing 302 to allow additional smoke to escape from the interior of the orb 102. The cover 300, the central housing 302 and the orb base 306 are preferable made of a plastic material that meets the plastics flammability standard UL 94 V0-V1, as released by Underwriters Laboratories of the United States, such that it can handle high temperature from the incense and perfume heating components. It should be noted that the shape of the outer surfaces of the cover 300, orb base 306, and in particular. the central housing 302 are exemplary, and each may have other shapes, such as cylindrical, and further, the use of the term orb should not be considered as limiting the smart electric incense and perfume burner 100 to the shape shown in the drawings. The number and size of the openings 108 can also be varied, as desired.

Figures 4, 5:
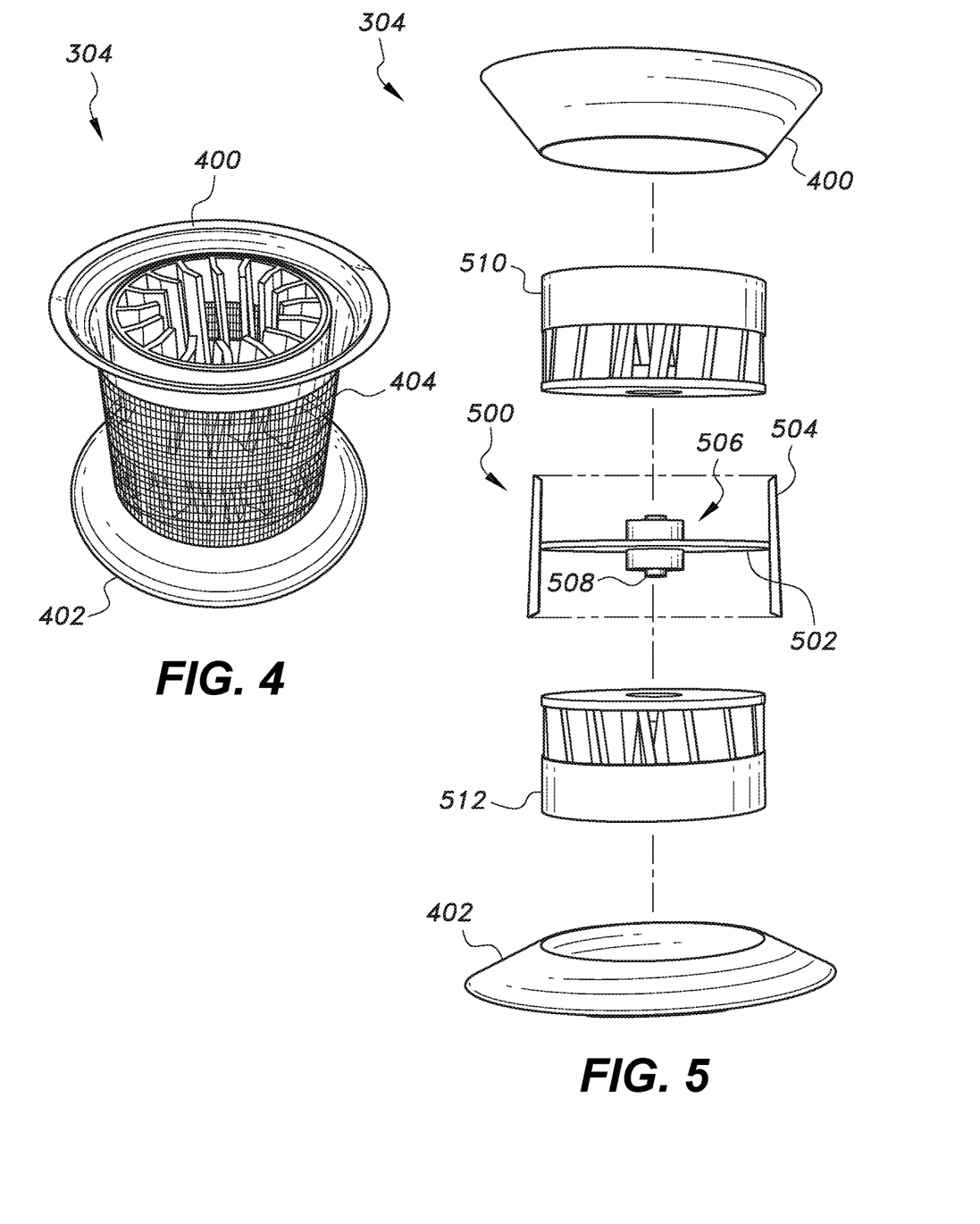
FIG. 4 is a perspective view of a fan assembly of the smart electric incense and perfume burner of FIG. 1.
FIG. 5 is an exploded perspective view of the fan assembly of FIG. 4, the mesh screen being omitted.

The structure of the dual fan assembly 304 is shown in FIGS. 4-5. The dual fan assembly 304 includes an upper frustoconical fan diffuser 400, a lower frustoconical fan diffuser 402 and an outer, cylindrical, protective mesh housing 404 that extends between the upper fan diffuser 400 and the lower fan diffuser 402. The protective mesh housing 404 is not shown in FIG. 5 to allow viewing the internal components of the dual fan assembly 304. A fan support bracket 500 is attached to the outer, cylindrical, mesh housing 404 and includes an outer cylindrical flange 504 attached to the outer, cylindrical, mesh housing 404, and a central disc-shaped support plate 502 centrally mounted in the outer cylindrical flange 504. A brushless DC motor 506 is centrally mounted through the center of the support plate 502 and includes a drive shaft 508. The top of the drive shaft 508 is attached to and drives a first, upper fan 510, while the bottom of the drive shaft 508 is attached to and drives a second, lower fan 512. The fans 510, 512 are centrifugal fans with helical vertical blades that direct smoke from the lower chamber 200 out of the plurality of openings 108 and the circular slot 120.

Figure 6:
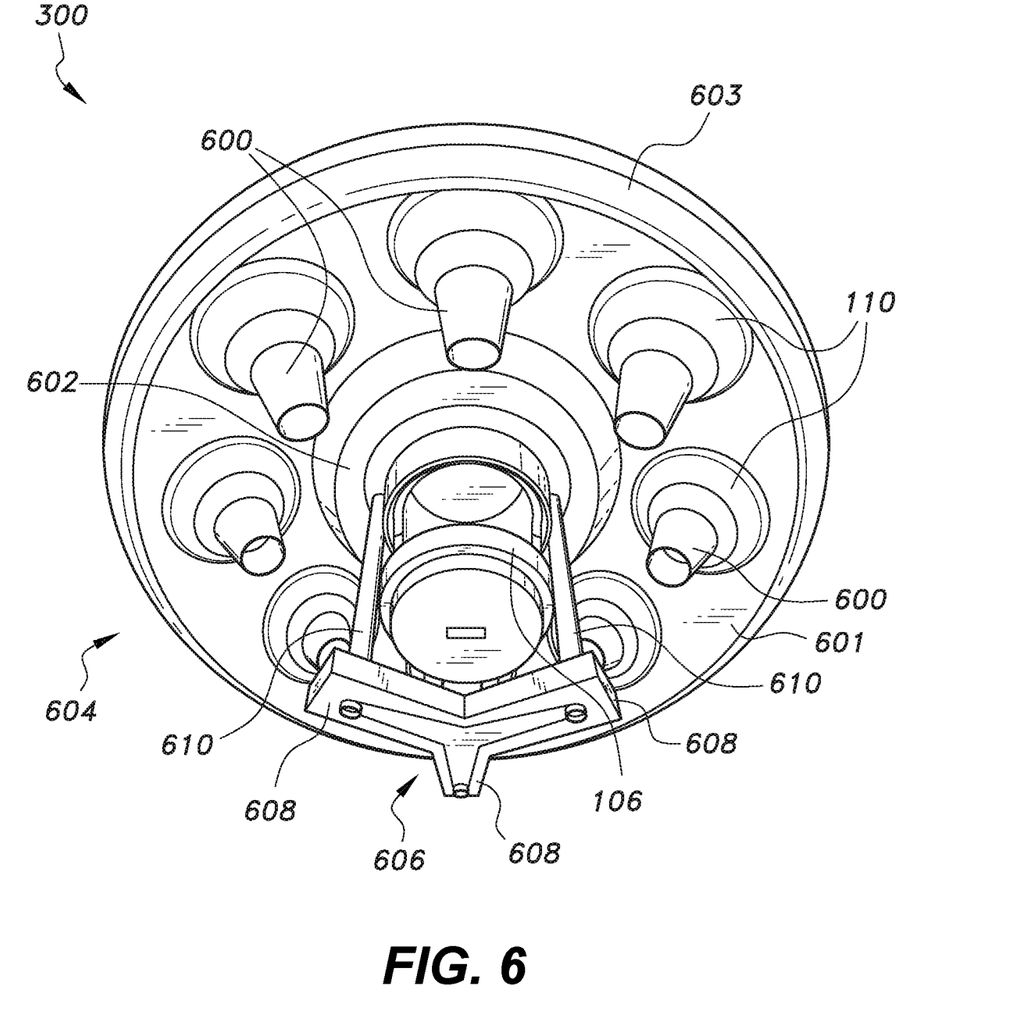
FIG. 6 is a perspective view of the upper cover portion of the smart electric incense and perfume burner of FIG. 1, shown from below with the upper chamber compartment in a lowered position.
Figure 7:
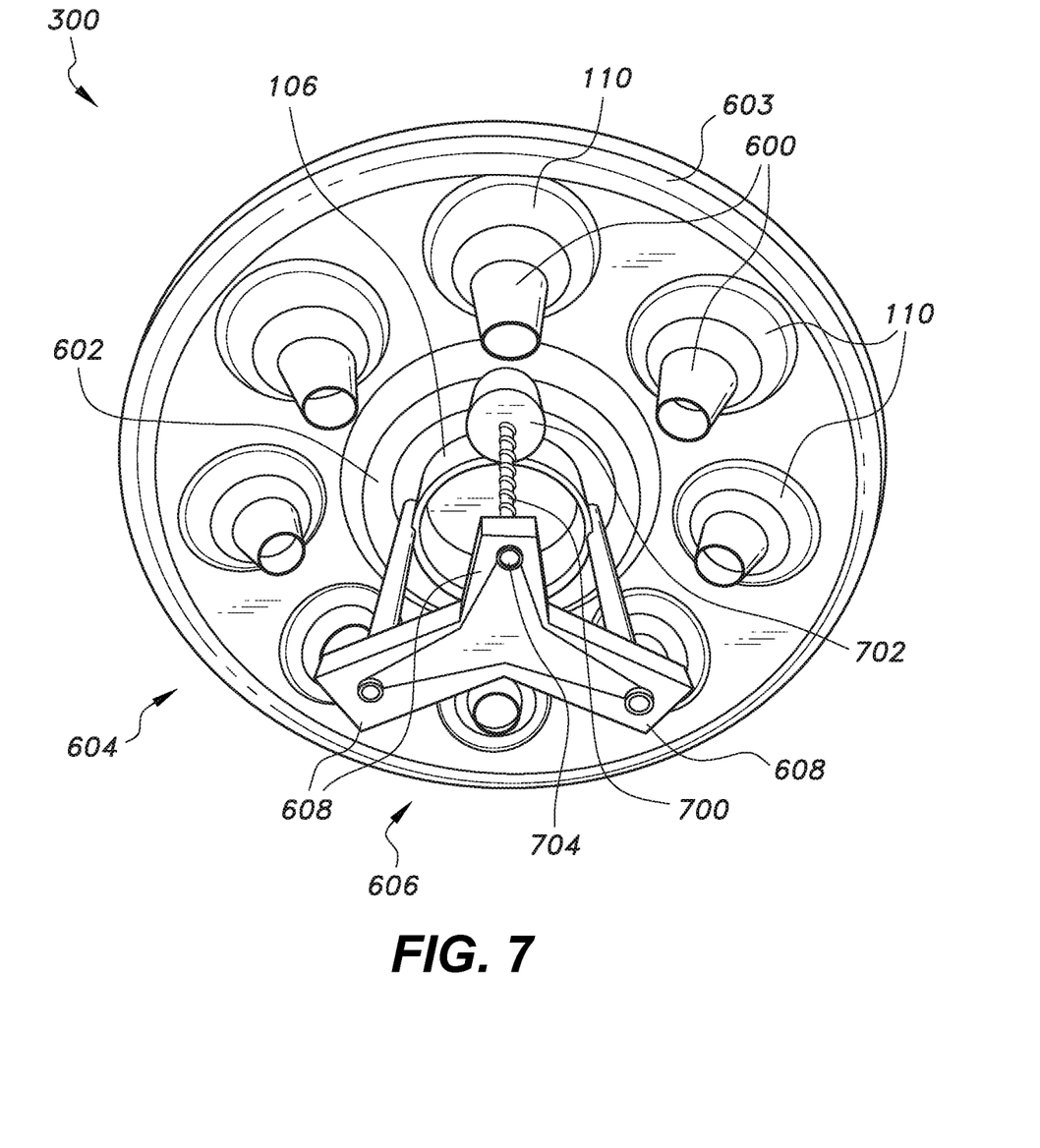
FIG. 7 is a perspective view of the upper cover portion of FIG. 6, shown from below with the upper chamber compartment in a raised position.

The structure extending from the bottom of the cover 300 is shown in FIGS. 6-7. The cover 300 includes the top circle of openings 108, as shown in FIGS. 1-3. The bottom of the hollow, frustoconical, acrylic LED housings 110 include hollow, frustoconical, extensions 600 attached thereto. The extensions 600, provide support for the stems of flowers (or other elongate decorations) to maintain them in a more up-right position within the openings 108. The cover 300 includes a partially spherical bottom surface 601, with a descending ring-shaped surface 602 at its center and a flat annular flange 603 for engaging the top of the central housing 302. The upper chamber 106 is retractable through a central hole in the cover 300 and is shown in its retracted, lower position in FIG. 6, and in its extended, raised position in FIG. 7.

Figure 8:
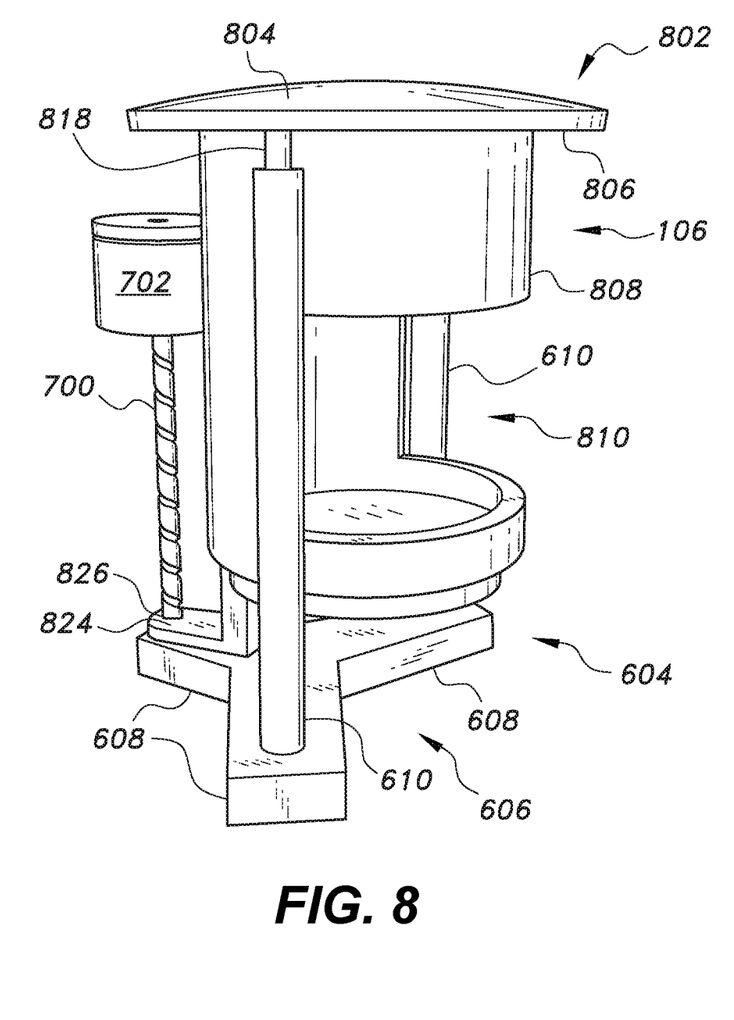
FIG. 8 is a perspective view of the upper chamber compartment of FIGS. 6-7, shown with the upper chamber compartment in the lowered position.

The structure of the upper chamber 106 and the mechanism 604 for raising and lowering the upper chamber 106 are shown in FIGS. 6-8. The upper chamber 106 includes a chamber cover 802 that has a spherically shaped upper surface 804 and a planar disc-shaped lower surface 806. The upper chamber 106 further includes a hollow, cylindrical, chamber housing 808 attached centrally to and extending downward from the lower surface 806 of the chamber cover 802. The housing 808 includes an opening 810 wherein a portion of the cylindrical wall is omitted or cut away. The opening 810 allows for the insertion of a liquid perfume capsule 900 when the upper chamber 106 is in its raised, extended position, as described below with respect to FIG. 9.

The mechanism 604 for raising and lowering the upper chamber 106 includes a base 606 having three legs 608 attached to one another at their proximate ends and extending 120° from each other. The distal ends of two of the legs 608 include hollow guide tubes 610 attached to and extending upward therefrom. Each of the guide tubes 610 telescopically houses a guide rod 818 (one shown in FIG. 8) that extends downward from the lower surface 806 of the chamber cover 802 approximately halfway between the chamber housing 808 and the outer edge of the chamber cover 802. The guide tubes 610 and guide rods 818 provide lateral stability, while still allowing up and down translation of the upper chamber 106. The distal end of the third leg 608 of the base 606 is supported by a rotating threaded rod 700 that is rotatably connected at its lower end to the distal end of the third leg 608 using a bearing or bushing 704. The upper end of the rotating threaded rod 700 is connected to and supported by the drive shaft of an electric motor 702. The electric motor 702 is attached to and supported by the descending ring-shaped surface 602 of the cover 300. The electric motor 702 and threaded rod 700 provide vertical stability and additional lateral stability for the base 606. A tab 824 is attached to or integral with the bottom of the chamber housing 808 and includes a threaded bore 826 that the threaded rod 700 extends through. When the driveshaft of the motor 702 is driven in a first direction, the tab 824, the chamber housing 808, the chamber cover 802 and the guide rods 818 are driven upward, and when the driveshaft of the motor 702 is driven in a second, opposite direction, the tab 824, the chamber housing 808, the chamber cover 802 and the guide rods 818 are driven downward. In this manner, the mechanism 604 for raising and lowering the upper chamber 106 acts as a linear actuator.

Figure 9:
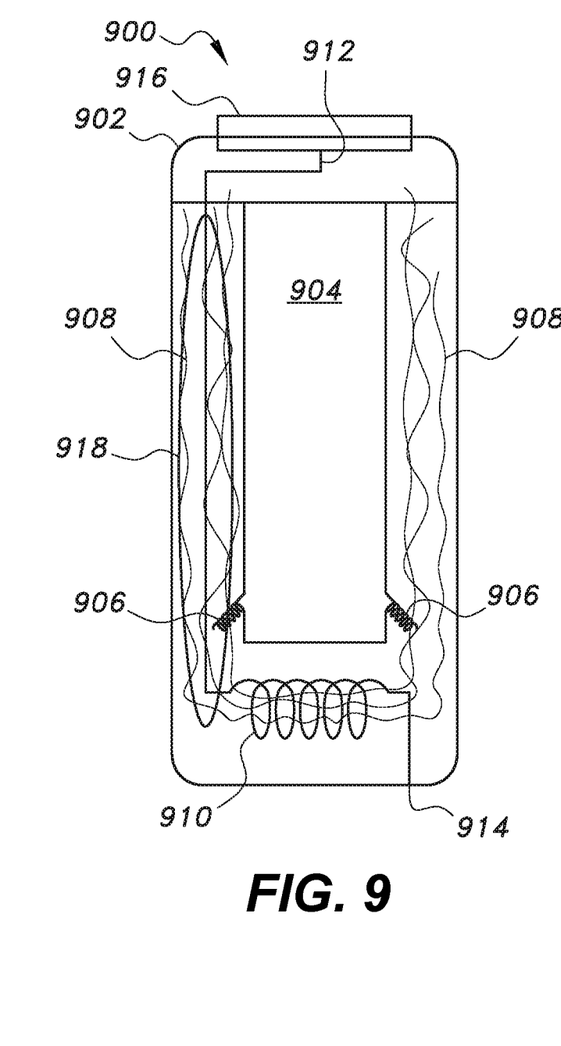
FIG. 9 is a diagrammatic side view of a capsule for insertion into the upper chamber compartment of FIGS. 6-8.

The details of the liquid perfume capsule 900 are shown in FIG. 9. The capsule 900 includes an outer cylindrical housing 902 that contains a cylindrical perfume liquid reservoir 904 with two lower openings 906, each opening 906 having a cotton wick 908 extending therefrom. The cotton wick 908 extends completely around the cylindrical perfume liquid reservoir 904, between the reservoir 904 and the outer housing 902. An electric resistance heating coil 910 is disposed within the cotton wick 908, such that the cotton wick 908 extends from within the coil 910 to outside of the coil 910 for maximum heating of the cotton wick 908. The ends of the coil 910 include a top 912 and bottom 914 electrode. The bottom electrode 914 has a magnetic connection with a metal pin (not shown) that inserts into a bore (not shown) in the bottom of the upper chamber housing 808 to make electrical connection with the microcontroller 1012, described below. The top electrode 912 is connected to a capsule cap 916. The capsule cap 916 includes a button-like mechanism (not shown) that opens the cap when pressed so that the perfume scent can escape from the outer housing 902 casing, while also connecting the top electrode 912 to the electrical system of the orb 102 to activate the coil 910 to heat the wick 908 and release the perfume therefrom. A protective cover 918 covers the coil wire extending though the wick 908 from the coil 910 to the electrode 912.

The structure of the orb base 306 and the lower chamber 200 are shown in FIGS. 10-14. The upper portion 1000 of the orb base 306 is in the shape of a lower portion of a sphere, such that the cover 300, the central housing 302 and the orb base 306 form a substantially spherical housing, with the lower 10% of the sphere truncated to form a planar horizontal bottom surface 1100. The planar horizontal bottom surface 1100 makes the orb 102 stable when it is placed on a flat surface, without the use of the pedestal 104. The top of the orb base 306 has a ring-shaped inwardly extending flange 1002 that is attached to the circular top edge 1004 of the upper portion 1000 of the orb base 306. The flange 1002 provides a flat surface for the central housing 302 to rest upon.

Figures 10, 11:
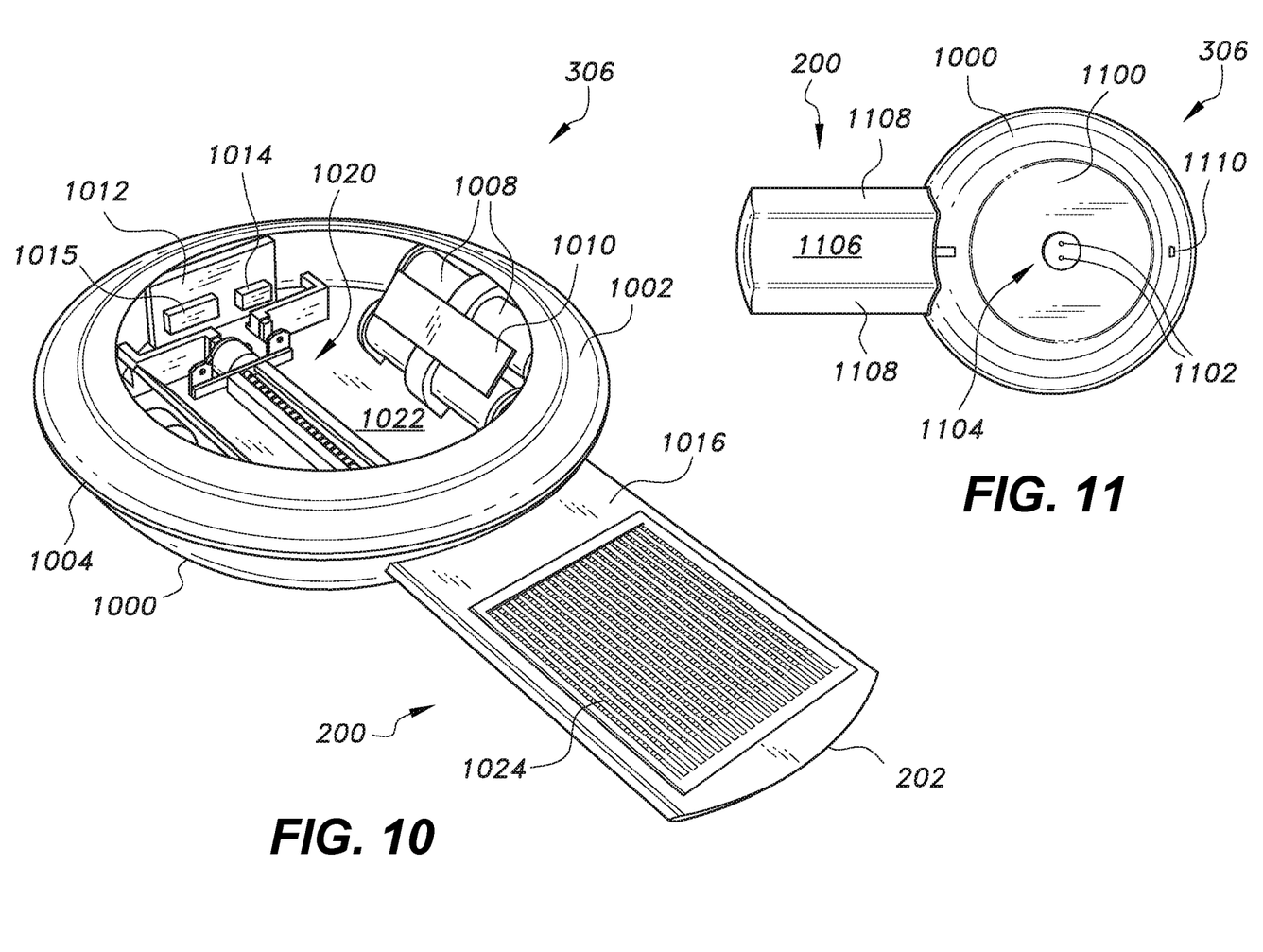
FIG. 10 is a perspective view of the compartment in the lower portion of the smart electric incense and perfume burner of FIG. 1, as viewed from above the lower portion.
FIG. 11 is a bottom view of the lower portion of the burner of FIG. 10.
Figure 12:
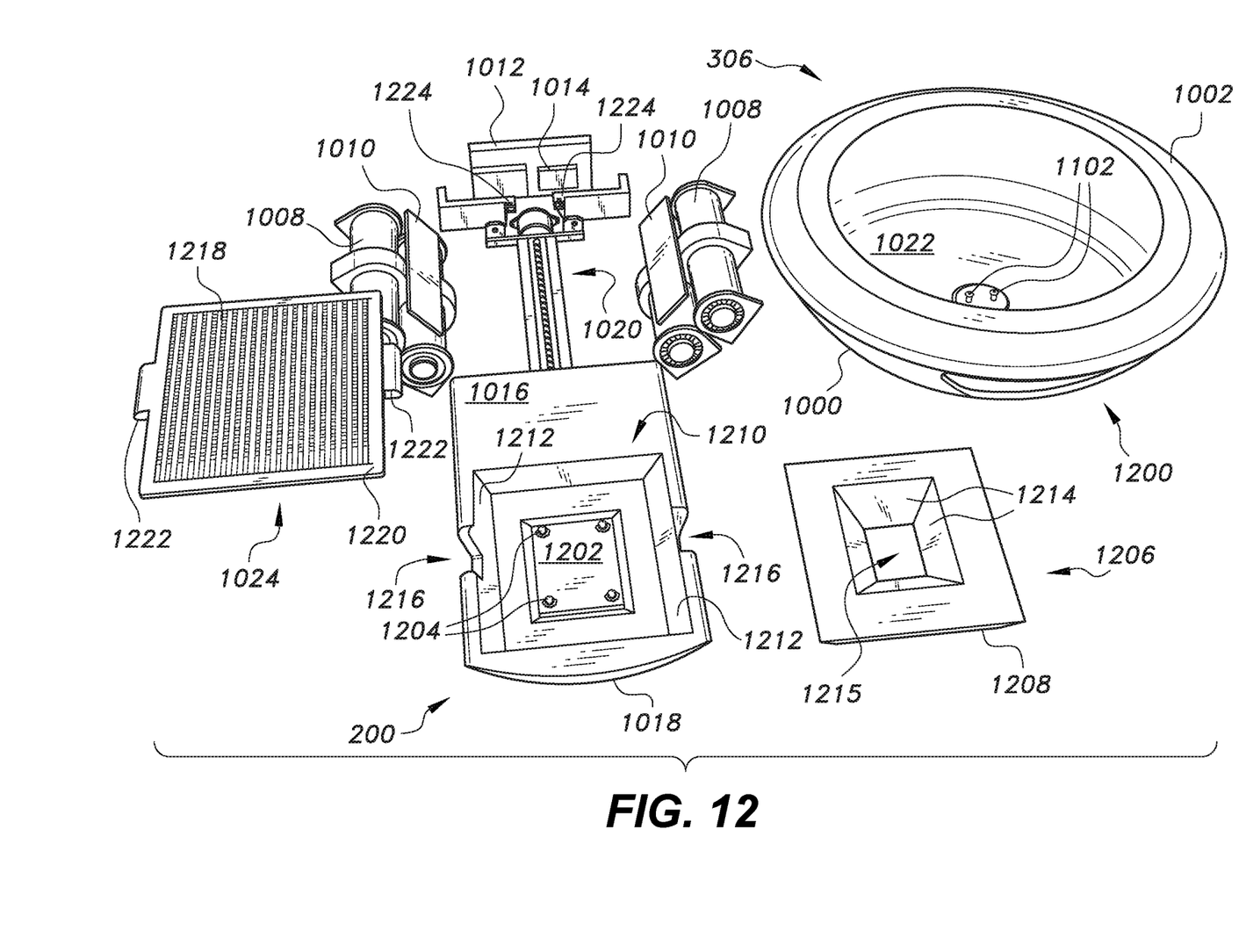
FIG. 12 is an exploded perspective view of the lower portion of the burner of FIG. 10.

The interior of the orb base 306 includes eight high-temperature, rechargeable lithium batteries 1008 and two battery management systems (BMS) 1010 mounted on the sides of the orb base 306 and partially covered by the flange 1002. The interior of the orb base 306 also includes a microcontroller 1012 and sensors 1014 that detect the temperature and smoke density. A plurality of switches 1015 are controlled by the microprocessor 1012 to provide the operating voltages for the various components of the smart electric incense and perfume burner 100. In one embodiment, the switches 1015 are metal oxide semiconductor field effect transistors (MOSFETs). The microcontroller 1012 adjusts the incense temperature/voltage and the speed/voltage of the fans 510, 512 based on the data from the sensors 1014. In addition, when the temperature sensed is above a predetermined safe limit, the microcontroller 1012 inhibits the linear actuators 604, 1020 (described below) from opening the chambers 106, 200. A three-axis or six-axis gyroscopic accelerometer may be included with the microcontroller 1012 and detects the tilting of the orb 102 and sends a signal to the microcontroller 1012 for automatic electrical shutdown of the orb 102. The microcontroller 1012 also includes Wi-Fi and Bluetooth communication devices such that the smart electric incense and perfume burner 100 can be turned on and controlled remotely through a smart phone app or using smart home devices, such as Google Home or Amazon Alexa. The batteries 1008 are electrically connected (through their associated BMS 1010) to the microcontroller 1012 and to two electrical contacts or pins 1102 that extend through the bottom surface 1100 of the orb base 306 in a central circular recess 1104 in the bottom surface 1100 for charging by the pedestal 104, as explained further below. The batteries 1008 can also be charged without the base 104 thru a USB 3.1 Type-C Cable or newer fast charging cable connected to a USB 3.1 Type C SMT jack 1110 on the upper portion 1000 of the orb base 306. Once charged, the orb 102 can operate without the use of the pedestal 104 or a charging cable.

The lower chamber 200 is in the form of an electrically retractable drawer that extends and retracts through an opening 1200 (FIG. 12) in the upper portion 1000 of the orb base 306. The lower chamber 200 includes a planar top surface 1016, a planar bottom surface 1106 and curved side surfaces 1108. The distal end 202 of the chamber 200 is curved, such that the distal end 202 is flush with the upper portion 1000 of the orb base 306 when the chamber 200 is closed to provide a continuous spherical surface therewith (see FIG. 2). A mechanism 1020 for extending and retracting the chamber 200 is mounted to the bottom surface 1022 of the interior of the orb base 306. The top surface 1016 of the lower chamber 200 has a protective mesh cover 1024 that prevents any solid incense debris from coming out of the lower chamber 200.

Figure 13:
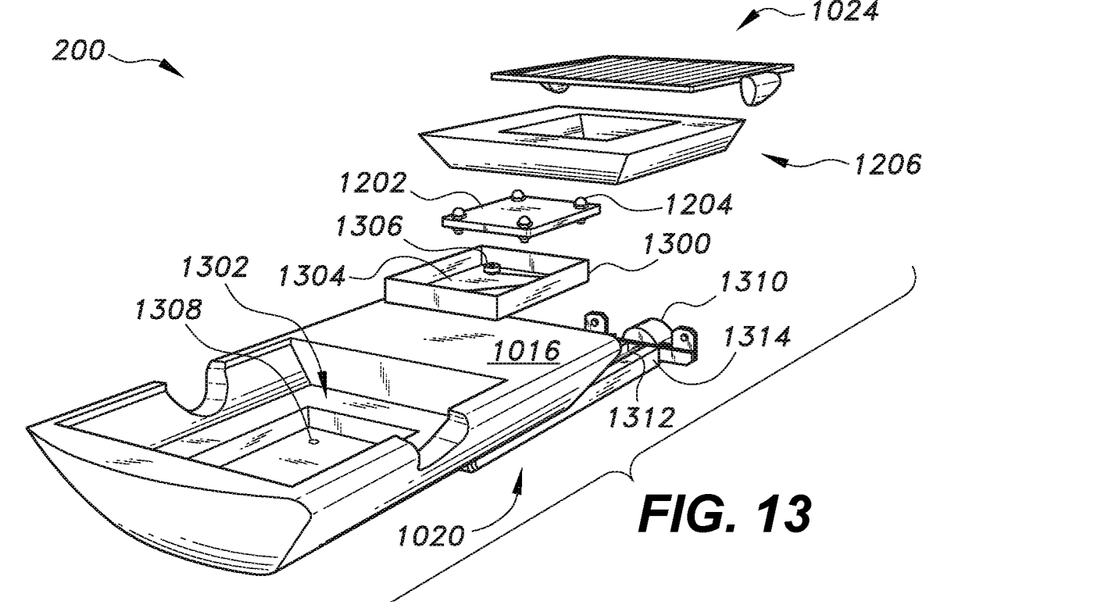
FIG. 13 is an exploded perspective view of the lower compartment from the lower portion of the burner of FIG. 10 as seen from the front of the compartment.
Figure 14:
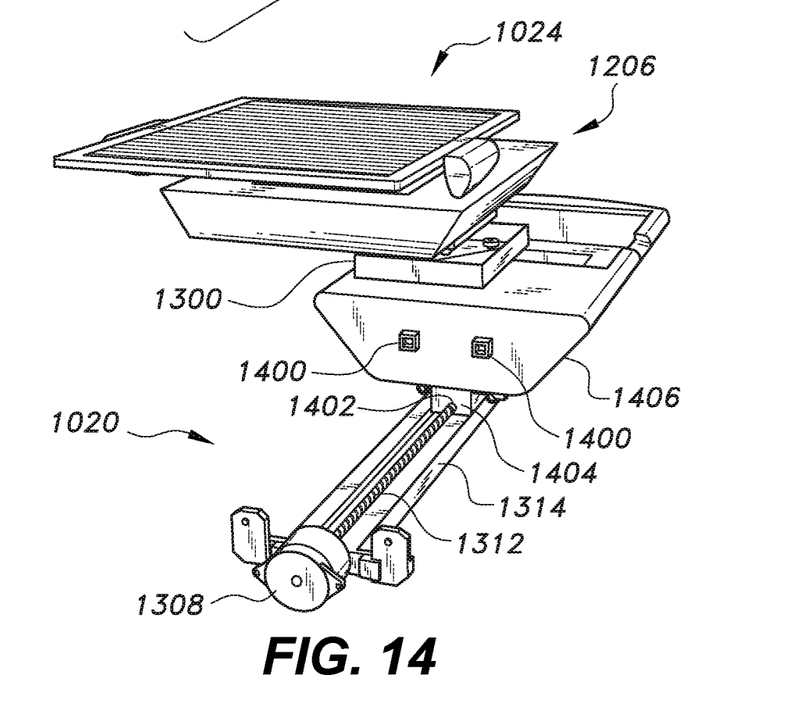
FIG. 14 is an exploded perspective view of the lower compartment from the lower portion of the burner of FIG. 10 as seen from the rear of the compartment.

As best seen in FIGS. 12-14, the interior of the lower chamber 200 includes a lower rectangular protective tray 1300 that fits inside a deep central rectangular recess 1302 in the bottom of the interior of the lower chamber 200. The tray 1300 includes a layer of heat resistant tape 1304 and four electrical connectors 1306 that extend through the layer of heat resistant tape 1304 and the bottom of the tray 1300, adjacent to the corners of the tray 1300. A solid incense heater 1202 is positioned within the tray 1300 and includes four conductive fasteners 1204 that align with and contact the four electrical connectors 1306 in the bottom of the tray 1300. The details of the solid incense heater 1202 are described below with respect to FIG. 17. The rectangular recess 1302 includes four (one shown in FIG. 13) electrical contacts 1308 for providing electrical power to the four conductive fasteners 1204 via the four electrical connectors 1306. The electrical contacts 1308 are connected to two lower chamber conductive pins 1400, (FIG. 14). The lower chamber conductive pins 1400 are connected to the microcontroller 1012 via two power transfer contacts 1224 when the lower chamber 200 is in its retracted position within the orb base 306.

The tray 1300 is surrounded by a frame 1206 that has sloping exterior sidewalls that mate with sloping interior walls 1212 in a shallow rectangular recess 1210 that surrounds the deep central rectangular recess 1302 in the bottom of the interior of the lower chamber 200. The frame 1206 has sloping interior sidewalls 1214 that slope down to a central rectangular opening 1215 to allow the dispersion of the incense smoke as it rises through the opening 1215. The sloping interior walls 1212 include a U-shaped cut-out or notch 1216 to assist a user when they wish to remove the frame 1206. The protective mesh cover 1024 includes a central metal mesh 1218 surrounded by a solid frame 1220. The sides of the solid frame 1220 include tabs 1222 that snap into the tops of the notches 1216 to hold the cover 1024 in place over the frame 1206.

The structure of the mechanism 1020 for extending and retracting the chamber 200 is best seen in FIGS. 13-14. The mechanism 1020 is a linear actuator that includes an electrical motor 1310 that is electrically connected to and controlled by the microcontroller 1012. The drive shaft of the motor is connected to a threaded rod 1312 that extends along the interior of an actuator frame 1314. The threaded rod 1312 extends through a threaded bore 1402 in a tab 1404 that is connected to and extends downward from the inside edge 1406 of the bottom surface 1106 of the lower chamber 200. The distal end of the threaded rod 1312 is rotatably mounted in the distal end of the actuator frame 1314 (not shown). When the electrical motor 1310 is driven in a first direction, the chamber 200 is extended out of the opening 1200 in the upper portion 1000 of the orb base 306 to a point where the chamber 200 is fully extended (FIGS. 3, 10 and 11). When the electrical motor 1310 is driven in a second, opposite direction, the chamber 200 is retracted into the opening 1200 in the upper portion 1000 of the orb base 306 to a point where the chamber 200 is fully retracted and the distal end 202 of the chamber 200 is flush with the upper portion 1000 of the orb base 306 to provide a continuous spherical surface therewith, (see FIG. 2).

In addition to being controlled remotely using Wi-Fi or Bluetooth communication, the various functions of the smart electric incense and perfume burner 100 may be controlled by the programmable pushbuttons 107, 109. For example, the pushbutton 107 may be programmed to raise/lower the upper chamber 106 when pressed a single time, and the pushbutton 109 may be programmed to one extend/retract the lower chamber 200, when pressed a single time. To control other functions, both pushbuttons 107, 109 act as multi-functional input switches when pressed multiple times, or for extended periods of time, or both, based on the programming of the microcontroller 1012, as is known in the art. For example, when the temperature sensed is above a predetermined safe limit, and the microcontroller 1012 inhibits the opening of the chambers 106, 200, the chambers may be opened by depressing the appropriate pushbutton(s) 107 and/or 109 for an extended period of time, such as 10 seconds.

The structure of the pedestal 104 is shown in FIGS. 1, 2, 15 and 16. The pedestal 104 acts as the multimedia and charging dock for the orb 102 and includes a concave bay 1500 with an upper partially spherical surface 1502 and a lower horizontal flat surface 1504 for receipt of the orb 102. The upper partially spherical surface 1502 and the lower horizontal flat surface 1504 mate with the lower surfaces of the orb 102, as described further below. The rear of the pedestal 104 includes a curved opening or notch 210 in the concave bay 1500, to allow the lower chamber 200 to extend therethrough in its extended position. An AC power cable 112 electrically connects the pedestal 104 to an AC power source using a conventional AC plug 113 at its distal end. The proximate end of the power cable 112 may include a plug 206 for insertion into a jack 208 in the pedestal 104. The pedestal 104 may also include optional features, such as: Wi-Fi and Bluetooth devices (not shown) such that the smart electric incense and perfume burner 100 can be turned on and controlled remotely thru a smart phone app or using smart home devices like Google Home or Amazon Alexa; as well as a media player (not shown) for radio, IOS and Android devices. In addition, the pedestal 104 includes an AC/DC converter and a relay component (not shown) for providing charging DC power for the orb 102.

Figure 15:
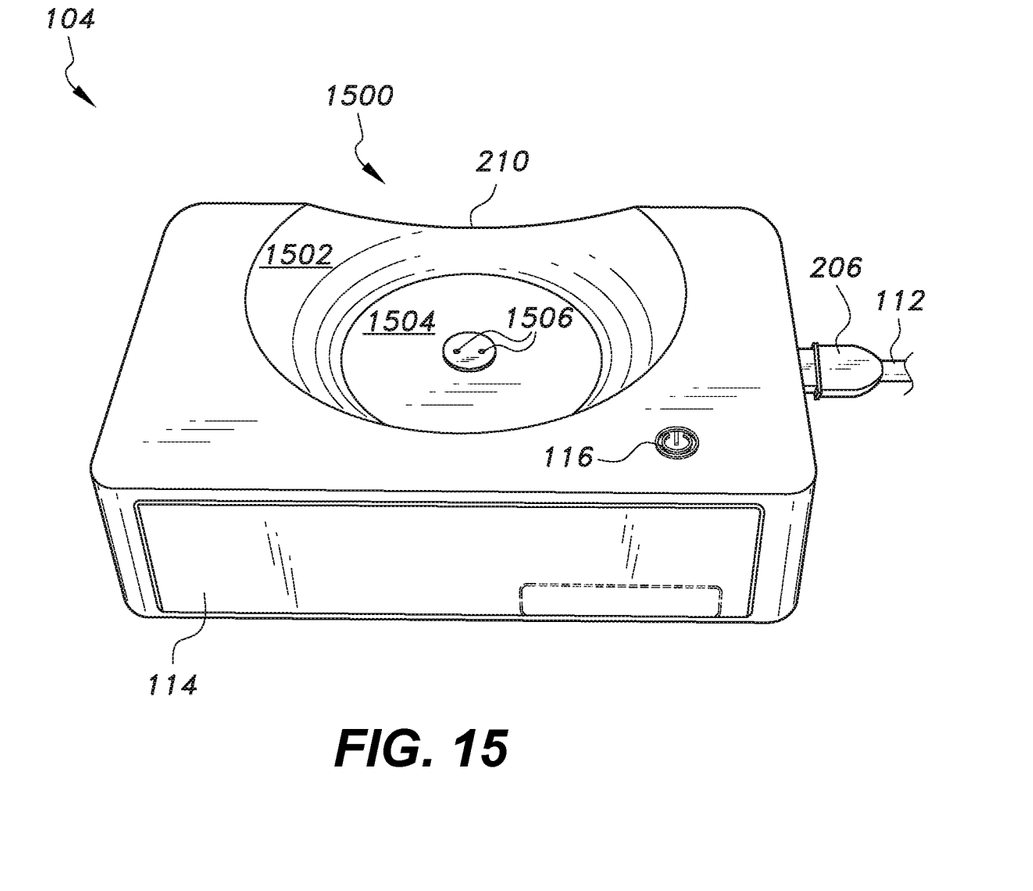
FIG. 15 is a perspective view of the pedestal of the smart electric incense and perfume burner of FIG. 1, as seen from the front of the pedestal.

The top surface of the pedestal 104 has an on/off button 116 mounted thereon. By pressing button 116, the input of the AC/DC converter is connected to the outlet 208 to activate the AC/DC converter. As is known in the art, the power button 116 may connect only one phase of the power source, while the other phase is not switched. In some embodiments, the power button 116 activates/deactivates a relay component, which connects/disconnects one or both phases of the power source with the input of the AC/DC converter. The DC output of the AC/DC converter is connected to two electrical contacts or pins 1506 at the center of the lower horizontal flat surface 1504 for connection to the electrical pins 1102 of the orb 102 power supply, as described above.

Figure 16:
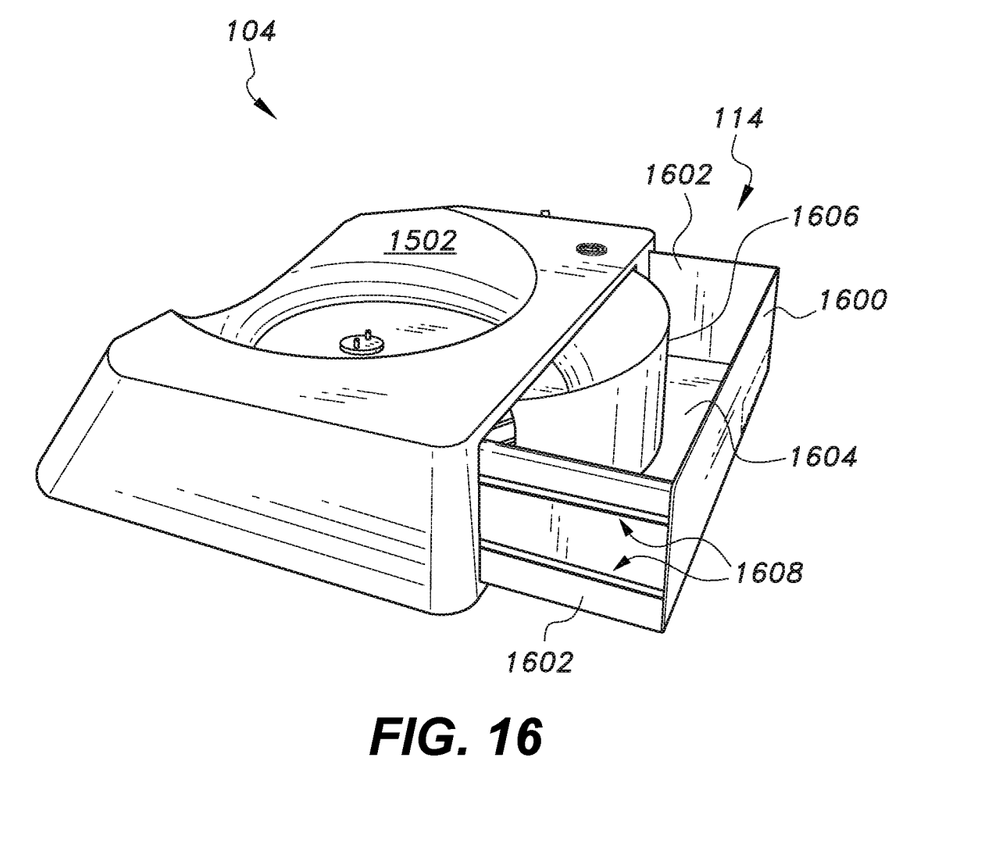
FIG. 16 is a perspective view of the pedestal of the smart electric incense and perfume burner of FIG. 1, showing an optional incense storage compartment in an open position.

The pedestal 104 may also include an optional incense storage drawer 114. As best seen in FIG. 16, the drawer 114 includes a flat planar front wall 1600 that is flush with the front wall of the pedestal 104 when the drawer 114 is closed. The drawer 114 also includes planar side walls 1602 and a planar bottom panel 1604 that are connected at right angles to the planar front wall 1600, as is known in conventional drawers. The planar side walls 1602 may also include drawer slides 1608 to allow the drawer 114 to more fully open. The rear wall 1606 of the drawer 114 is rounded to provide clearance for the upper partially spherical surface 1502, while maximizing the storage space of the drawer 114. It should be noted that the external shape of the pedestal 104 is not limited to the shape shown, but can have other shapes, so long as the upper partially spherical surface 1502 and the lower horizontal flat surface 1504 are provided for receipt of the orb 102. It should be further noted that the upper partially spherical surface 1502 and the lower horizontal flat surface 1504 may be replaced with other-shaped surfaces, so long as they mate with the shape of the lower outer surface(s) of the orb base 306.

Figure 17:
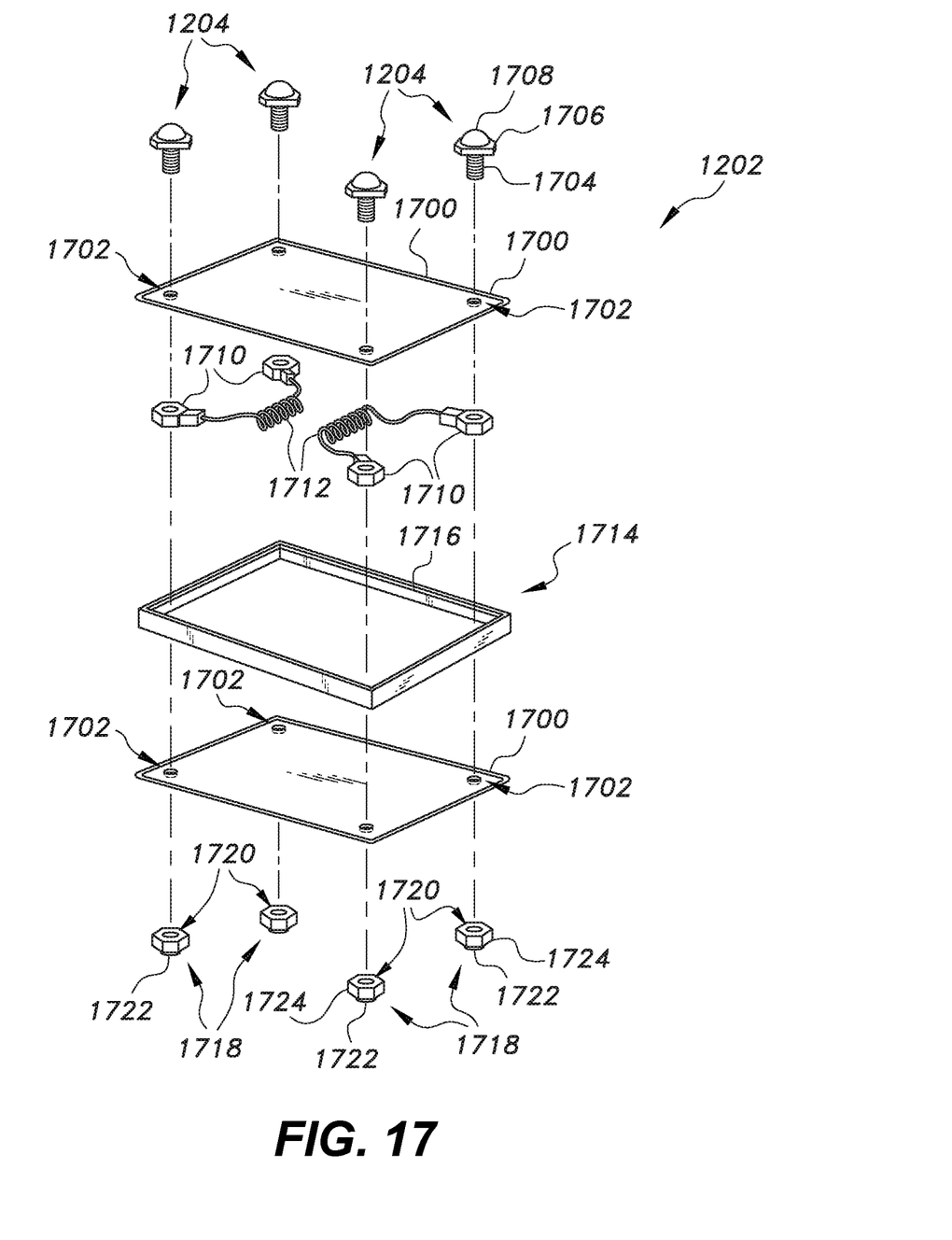
FIG. 17 is an exploded perspective view of the solid incense heater shown in FIGS. 12 and 13.

The solid incense heater 1202 is shown in FIG. 17, in an exploded view. The solid incense heater 1202 includes two mica sheets 1700 with through holes 1702 adjacent their corners. The four conductive fasteners 1204 are bolts having a threaded shaft 1704, a central hex-shaped section 1706 for engagement by a tool, such as a wrench, and a hemispherical electrical contact section 1708. The electrical heaters include two electrical heaters, each having two conductive washers 1710 and a heating coil 1712 extending between and electrically connected to the two conductive washers 1710. A steel central frame 1714 includes two opposed ledges 1716 (one shown) against which the mica sheets 1700 rest when the solid incense heater 1202 is assembled. The solid incense heater 1202 also includes four conductive nuts 1718. The four conductive nuts 1718 each include a central threaded blind bore 1720, a central hex-shaped section 1724 for engagement by a tool such as a wrench, and a hemispherical electrical contact section 1722. To assemble the solid incense heater 1202, the four conductive bolts 1204 are guided through: the holes 1702 in one of the mica sheets 1700; the conductive washers 1710; and the holes 1702 in the other mica sheet 1700 (after aligning the mica sheets 1700 on the ledges 1716 of the steel frame 1714). The bolts 1204 are then screwed into the threaded blind bores 1720 of the four conductive nuts 1718. It should be noted that while the shape of the solid incense heater 1202 is shown as generally rectangular, other shapes, number of holes, heaters and fasteners are also possible. In addition, while the electrical contact sections 1708, 1722 are shown as hemispherical, other shapes, such as cylindrical or conical, are possible. The electrical contacts 1308 (shown in FIG. 13) include top surfaces that have recesses that are shaped to accept the electrical contact sections 1708, 1722 and maximize the electrical contact surface area between the electrical contact sections 1708, 1722 and the electrical contacts 1308. In the embodiment shown, the recesses in the electrical contacts 1308 are hemispherical in shape (see FIG. 13). The bolts 1204 and nuts 1718 may be magnetic for increased adhesion between the electrical contact sections 1708, 1722 and the electrical contacts 1308.

The solid incense heater 1202 has separate utility outside of the smart electric incense and perfume burner 100 using a base (not shown) having a power supply or battery and a container similar to tray 1300 with contacts 1306 for providing electrical power to the electrical heaters. The symmetry of the solid incense heater 1202 allows it to be flipped such that either mica sheet 1700 may be on top for supporting the solid incense, if one of the mica sheets 1700 become damaged or worn. The materials of the solid incense heater 1202, as described above, are merely exemplary, and other high-temperature materials may be used, such as high-temperature glass or other insulation material for the sheets 1700, instead of mica. The solid incense heater 1202 is a replaceable component and can be provided to customers separately.

It is to be understood that the smart electric incense and perfume burner is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A solid incense heater, comprising:
    a plurality of conductive bolts, each of the conductive bolts having:
        a threaded shaft;
        a central hex-shaped section; and
        an electrical contact section;
    a first sheet of electrically nonconductive material having a plurality of holes therethrough;
    a second sheet of electrically nonconductive material having a plurality of holes therethrough;
    a frame disposed between the first and second sheets of electrically nonconductive material, the frame having two opposed ledges for receipt of the sheets of electrically nonconductive material;
    at least one electrical heater having two conductive washers and a heating coil extending between and electrically connected to the two conductive washers;
    a plurality of conductive nuts, each of the conductive nuts having:
        a central threaded blind bore;
        a central hex-shaped section; and
        an electrical contact section, the threaded shafts of the conductive bolts extend through corresponding ones of the holes in the first and second sheets of electrically nonconductive material and the at least two conductive washers into the central threaded blind bores of the conductive nuts.

\* \* \* \* \*